(12) United States Patent
Ross

(10) Patent No.: US 9,486,609 B2
(45) Date of Patent: Nov. 8, 2016

(54) CLOG-PREVENTING VALVED CATHETER AND METHOD OF USING THE CATHETER

(71) Applicant: Christopher D. Ross, Pembroke Pines, FL (US)

(72) Inventor: Christopher D. Ross, Pembroke Pines, FL (US)

(*) Notice: Subject to any disclaimer, the term of this patent is extended or adjusted under 35 U.S.C. 154(b) by 544 days.

(21) Appl. No.: 13/948,593

(22) Filed: Jul. 23, 2013

(65) Prior Publication Data

US 2013/0303998 A1 Nov. 14, 2013

Related U.S. Application Data

(62) Division of application No. 12/561,191, filed on Sep. 16, 2009, now Pat. No. 8,512,291.

(60) Provisional application No. 61/097,425, filed on Sep. 16, 2008.

(51) Int. Cl.
*A61M 25/088* (2006.01)
*A61M 25/00* (2006.01)

(52) U.S. Cl.
CPC ..... *A61M 25/0082* (2013.01); *A61M 25/0009* (2013.01); *A61M 25/0068* (2013.01); *A61M 25/0069* (2013.01); *A61M 25/0075* (2013.01); *A61M 2025/0018* (2013.01); *A61M 2025/0079* (2013.01); *Y10T 29/49826* (2015.01)

(58) Field of Classification Search
CPC ............ A61M 2025/0018; A61M 2025/0079; A61M 25/0023; A61M 2210/0693
See application file for complete search history.

(56) References Cited

U.S. PATENT DOCUMENTS

| | | | | |
|---|---|---|---|---|
| 4,180,068 A * | 12/1979 | Jacobsen | ............... | A61B 17/34 604/164.01 |
| 4,449,532 A * | 5/1984 | Storz | ................. | A61B 1/00154 600/114 |
| 5,685,852 A * | 11/1997 | Turkel | ............... | A61B 17/3401 604/159 |
| 6,283,950 B1 * | 9/2001 | Appling | ............ | A61M 25/0075 600/585 |
| 6,524,299 B1 * | 2/2003 | Tran | .................. | A61M 25/0009 604/523 |
| 8,512,291 B2 * | 8/2013 | Ross | ................. | A61M 25/0068 604/164.01 |
| 2003/0073934 A1 * | 4/2003 | Putz | .................. | A61M 25/0668 600/585 |
| 2003/0093007 A1 * | 5/2003 | Wood | ................. | A61B 10/0275 600/564 |
| 2006/0206055 A1 * | 9/2006 | Ice | ..................... | A61B 17/3401 604/164.01 |
| 2007/0088295 A1 * | 4/2007 | Bankiewicz | ...... | A61M 25/0023 604/264 |
| 2010/0069855 A1 * | 3/2010 | Ross | ................. | A61M 25/0068 604/268 |

* cited by examiner

*Primary Examiner* — Aarti B Berdichevsky
(74) *Attorney, Agent, or Firm* — The Concept Law Group, P.A.; Erin A. Martin

(57) ABSTRACT

An anti-clogging catheter includes a hollow cannula defining a first interior diameter and a distal end defining a second interior diameter smaller than the first interior diameter. A solid stylet is movable within the fluid passageway and has an outer diameter substantially equal to the second interior diameter of the cannula, the stylet and cannula together defining (1) a closed fluid pathway that prevents neurological material from passing into the distal end of the cannula when the distal end of the stylet is extended into the distal end of the cannula and (2) an open fluid pathway that allows fluid to flow in a single contiguous path around the distal end of the stylet and out of the distal end of the cannula when the distal end of the stylet is retracted away from the distal end of the cannula and remains within the body of the cannula.

20 Claims, 15 Drawing Sheets

CLOG-PREVENTING VALVED CATHETER AND METHOD OF USING THE CATHETER

CROSS-REFERENCE TO RELATED APPLICATION

This application is a divisional of U.S. patent application Ser. No. 12/561,191 filed Sep. 16, 2009, which claims priority to U.S. Provisional Patent Application No. 61/097,425 filed Sep. 16, 2008; the prior applications are herewith incorporated by reference in their entirety.

FIELD OF THE INVENTION

The present invention relates generally to catheters, and more particularly relates to a catheter having a valve that prevents clogging of the catheter during insertion into tissue.

BACKGROUND OF THE INVENTION

Catheters are tubular passageways that, during a medical procedure, can be inserted into a body. Usually, the catheter is a thin, flexible tube; however, catheters can also be larger and usually more solid passageways. Catheters provide several functions, such as providing for delivery of fluids into the body, drainage of fluids out of the body, access by surgical instruments, removal of material out of the body, and more.

The process of inserting a catheter is referred to as "catheterization." A catheter left inside the body temporarily, e.g., a few hours or less, is referred to as an "acute" device. A catheter left inside the body for an extended period of time, e.g., days or weeks, is referred to as a "chronic" device.

One use of catheters is to provide delivery of drugs to treatment areas of the brain. These catheters are inserted through the soft brain tissue and guided to the location where pharmaceuticals or other fluid treatments are to be delivered. One problem that occurs during catheter insertion is clogging of the tip of the catheter fluid passageway. This clogging is, in large part, due to the extremely soft consistency of living brain tissue, which readily separates and pushes into the open end of the catheter.

Medically-therapeutic fluid is delivered through the catheter and to the treatment site by manual compression of a syringe or delivery by a mechanical pump. However, if the tip of the catheter is clogged, fluid cannot flow to the delivery site. The effect is that a sharp increase in pressure builds up inside the catheter. If the pressure releases all at once, i.e., the clog and fluid forcefully and instantly exit the tip of the catheter, tissue will likely be decimated, potentially causing damage, and in some cases severe damage, to the brain. Again, procedures to the brain are particularly susceptible to this type of damage as neural tissue is soft and can easily be destroyed by a pressurized liquid force.

Additionally, if the fluid does not exit the catheter properly, instead of being delivered to the treatment site, the fluid is forced away from the treatment site, travels back out of the catheter entry path (between the exterior of the catheter and the brain tissue), and out of the brain. This is highly undesirable, as neurological medicines are often delivered in very small doses and, therefore, measured with extremely high precision. Any loss of fluid destroys the dosage calculation, as it is virtually impossible to determine the amount of medicine lost or the contents of a portion of a compound lost. In addition, neurological medicines are often very expensive and, for at least this reason, losses should be avoided.

Although catheters used for neurological treatments are more susceptible to clogging than those used for treatment of other areas, clogging is still highly likely and can cause damage, can introduce uncertainty to treatment procedures, and can result in unnecessary financial waste.

Therefore, a need exists to overcome the problems with the prior art as discussed above.

SUMMARY OF THE INVENTION

The invention provides a clog-preventing valved catheter and method of using the catheter that overcomes the hereinafore-mentioned disadvantages of the heretofore-known devices and methods of this general type and that prevents clogging of a catheter during insertion into tissue.

With the foregoing and other objects in view, there is provided, in accordance with the invention, an anti-clogging catheter, that has a tubular cannula defining a fluid passageway, where the catheter is shaped and tipped to removably insert within and be removed from a human body. The cannula has a proximal end with a first interior surface that defines a first interior diameter and a distal end that has a second interior surface defining a second interior diameter that is smaller than the first interior diameter. A solid stylet is movable within the fluid passageway between the proximal end and the distal end and has an outer diameter substantially equal to the second interior diameter.

In accordance with a further feature of the present invention, the proximal end has a first exterior surface that defines a first exterior diameter and the distal end has a second exterior surface that defines a second exterior diameter that is smaller than the first interior diameter.

In accordance with a further feature of the present invention, the cannula includes a third interior surface between the first interior surface and the second interior surface, the third interior surface having a third interior diameter that is smaller than the first interior diameter and larger than the second interior diameter.

In accordance with the present invention, the cannula distally slopes between the first interior surface and second interior surface.

In accordance with another feature, an embodiment of the present invention includes a first exterior surface radially opposite the first interior surface, the first exterior surface having a distal end, a second exterior surface radially opposite the second interior surface, the second exterior surface having a proximal end, and a radiused exterior surface between the first exterior surface and the second exterior surface.

In accordance with another feature, an embodiment of the present invention also includes a radiused distal edge.

In accordance with yet another feature, an embodiment of the present invention includes an anti-clogging catheter shaped and tipped to removably insert within and be removed from a human body, where the catheter includes a hollow cannula having a distal end and an interior surface defining a cannula interior diameter and a cannula interior. A hollow tip is fixedly coupled to the interior surface of the cannula at the distal end, where the tip has an interior surface defining a tip interior diameter, with the tip interior diameter being smaller than the cannula interior diameter. A tip interior is fluidically connected to the cannula interior. A hollow orifice device is fixedly coupled to the interior surface of the tip and the orifice device has an interior surface that defines an orifice interior diameter, the orifice interior diameter being smaller than the tip interior diameter. An orifice interior is fluidically connected to the tip interior and a stylet is slidable within the cannula interior, the tip interior, and the orifice interior. The stylet has a distal portion with an outer diameter substantially equal to the orifice interior diameter such that biological material is prevented from passing into the orifice interior when the distal portion of the stylet is within the orifice interior.

With the objects of the invention in view, there is also provided a method for manufacturing an anti-clogging catheter that is shaped and tipped to removably insert within and be removed from a human body, where the method includes the steps of providing a cannula having an interior surface defining an interior diameter and a cannula interior, fixedly coupling a hollow tip to the interior surface of the cannula, the tip having an interior surface defining a tip interior diameter and a tip interior, to fluidically connect the tip interior to the cannula interior, the tip interior diameter being less than the interior diameter of the cannula, fixedly coupling a hollow orifice device to the interior surface of the tip, the orifice device having an interior surface defining an orifice interior diameter and an orifice interior, to fluidically connect the orifice interior to the tip interior, the orifice interior diameter being less than the tip interior diameter, and shaping a stylet to have a distal portion with an outer diameter substantially equal to the orifice interior diameter and slidably disposing the stylet in the cannula interior, the tip interior and the orifice interior such that biological material is prevented from passing into the orifice interior when the distal portion of the stylet is within the orifice interior.

In accordance with a further feature, embodiments of the present invention include a method for inserting an anti-clogging catheter into human tissue, where the method includes the steps of providing a catheter that includes a cannula having an interior surface defining an interior diameter and a cannula interior, a tip fixedly coupled to the interior surface of the cannula, the tip having an interior surface defining a tip interior diameter and a tip interior, to fluidically connect the tip interior to the catheter interior, the tip interior diameter being less than the interior diameter of the cannula, a hollow orifice device fixedly coupled to the interior surface of the tip, the orifice device having an interior surface defining an orifice interior diameter and an orifice interior, to fluidically connect the orifice interior to the tip interior, the orifice interior diameter being less than the tip interior diameter, and a stylet having a distal portion with an outer diameter substantially equal to the orifice interior diameter. The method further includes sliding the stylet through the cannula interior and the tip interior and into the orifice interior, the distal portion filling the orifice interior such that biological material is prevented from passing into the orifice interior, inserting at least the orifice device through tissue to a treatment location, and withdrawing the stylet from at least the orifice interior, thereby creating a fluid path from the cannula interior, through the tip interior, through the orifice interior, and into the treatment location.

Although the invention is illustrated and described herein as embodied in a clog-preventing valved catheter and method of using the catheter, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. The figures of the drawings are not drawn to scale.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
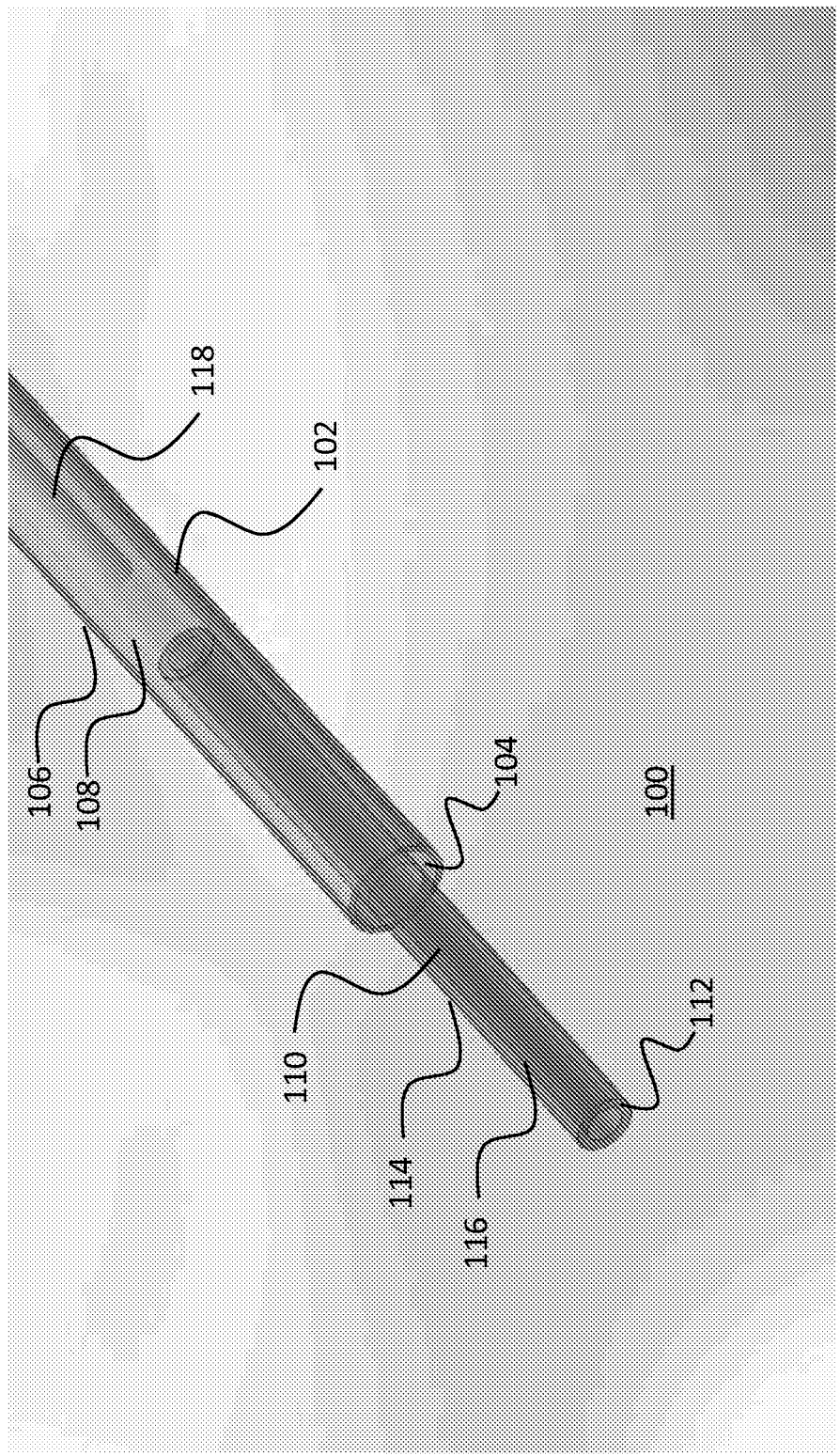
FIG. 1 is a fragmentary, transparent perspective view of an exemplary embodiment of an anti-clogging catheter device in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the catheter.

The present invention provides a novel and efficient anti-clogging catheter shaped to removably insert within a human body without clogging the tip with tissue being displaced by the moving catheter tip. Embodiments of the invention provide a leading tip with an interior fluid-passing diameter that is substantially the same size as an outer diameter of a solid stylet residing within an interior of the catheter. Thus, when the stylet is slid forward in the catheter, i.e., completely filling the interior of the leading tip, the tip cannot be filled with biological matter and is, therefore, incapable of being clogged.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components. The first example of an anti-clogging catheter 100, as shown in FIG. 1, includes a cannula 102. The cannula 102 is a tubular passageway that, depending on the material 104 used to form the cannula 102, is provided with varying levels of flexibility. The cannula 102 has an exterior surface 106 that defines an exterior diameter dimension and an interior surface 108 that defines an interior diameter dimension. The thickness of the cannula wall material 104 defines the difference between the exterior surface diameter and the interior surface diameter.

Inserted within and fixedly coupled to the interior surface 108 of the cannula 102 is a tip 110. As with the cannula 102, the tip 110 is a tubular passageway that, depending on the material 112 used to form the tip 110, is provided with varying levels of flexibility. The tip 110 has an exterior surface 114 that defines an exterior diameter dimension and an interior surface 116 that defines an interior diameter dimension. The thickness of the tip wall material 112 defines the difference between the exterior surface diameter and the interior surface diameter.

As can be clearly seen in FIG. 1, the tip interior diameter is less than the interior diameter of the cannula 102, inside which the tip 110 resides. Epoxy or other adhesive material can be used to fixedly couple the tip 110 to the cannula 102.

Figure 2:
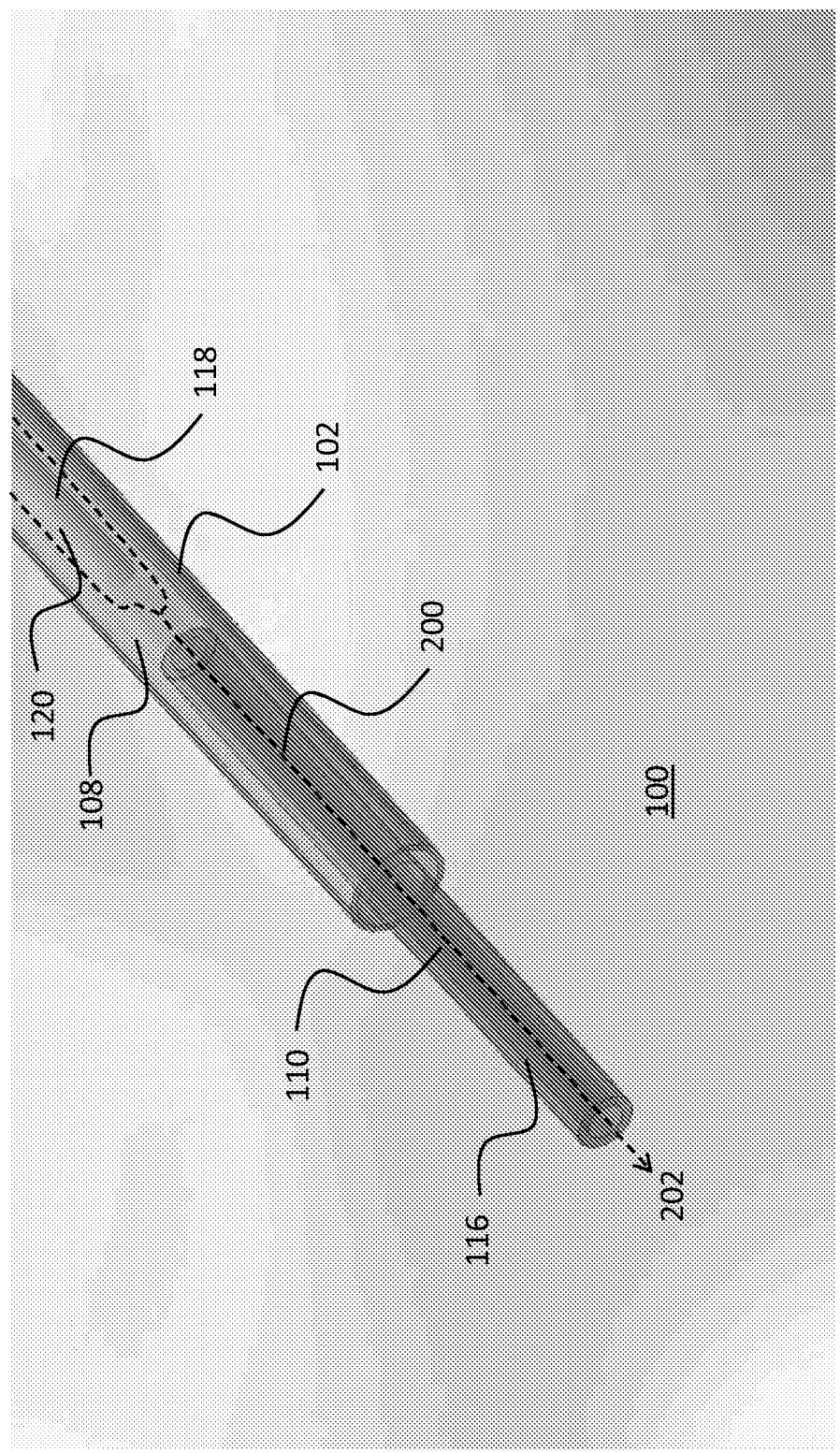
FIG. 2 is a fragmentary, transparent perspective view of the anti-clogging catheter device of FIG. 1 showing a fluid path through the catheter.

Also shown in the transparent view of FIG. 1, a solid stylet 118 is positioned within the interior of the cannula 102. "Stylets" are well-known in the art and, as used herein, is defined as a thin solid wire inserted into a catheter to maintain rigidity. The stylet 118 provides stiffness to the catheter as it is inserted into and through tissue. Shown in FIG. 2 is a fluid path 200 when the stylet 118 is disposed at the illustrated location within the cannula 102. The fluid path 200 starts within the gap between interior surface 108 of the cannula 102 and the outer surface 120 of the stylet 118, continues through the interior 116 of the tip 110, and out into the treatment area 202.

Figure 3:
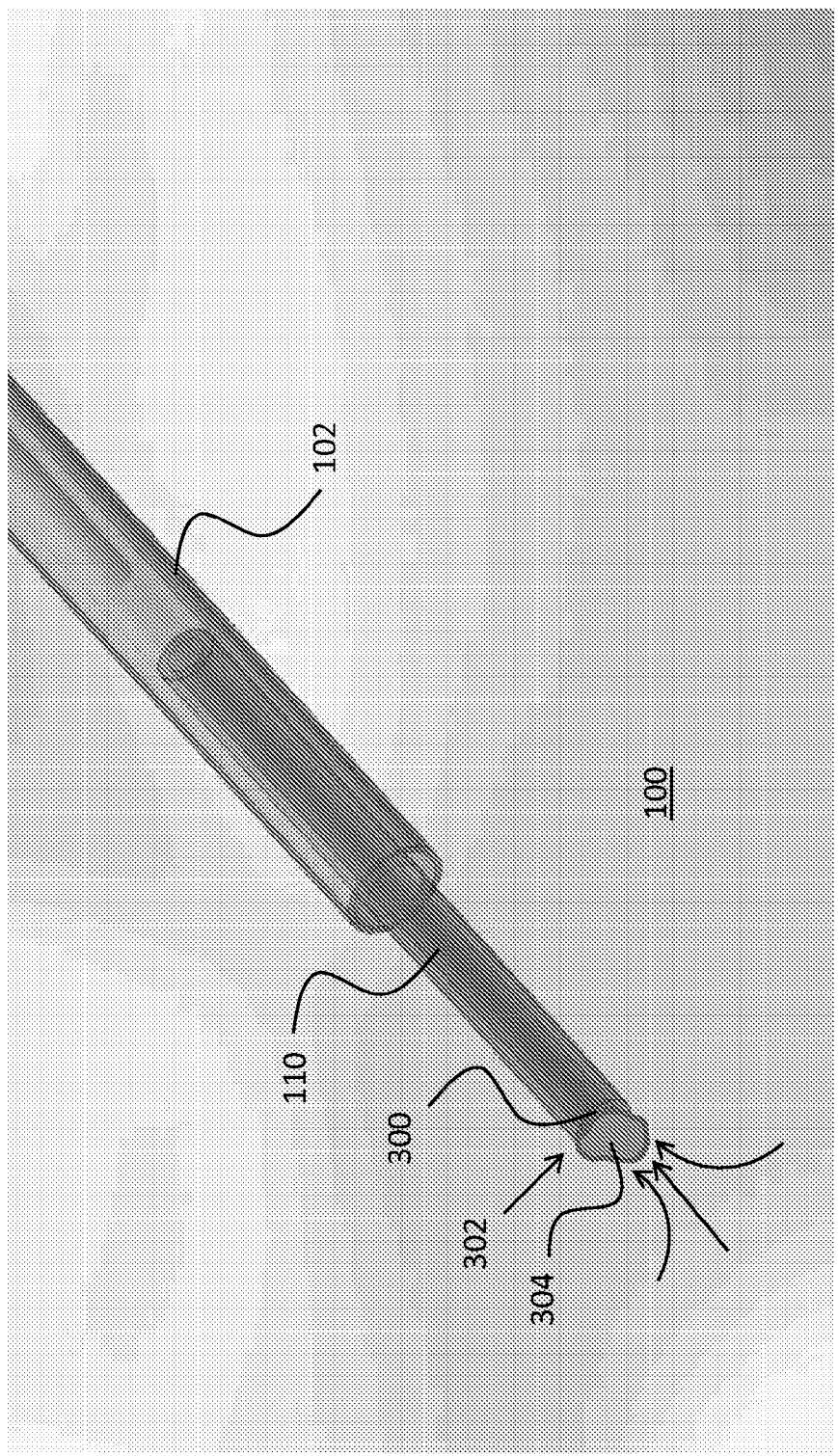
FIG. 3 is a fragmentary, transparent perspective view of the anti-clogging catheter device of FIG. 1 showing a biological material entry point within the catheter.

With the stylet's orientation within the cannula 102, as shown in FIGS. 1-3, during movement of the catheter 100 through tissue, the opening 300 in the distal end 302 of the tip 110 is susceptible of being filled with biological material 304, as shown in FIG. 3. This susceptibility is due to the fact that the passageway through the tip 110 is empty and provides an entry canal into the cannula 102, i.e., the reverse of the fluid flow 200 shown in FIG. 2.

Figure 4:
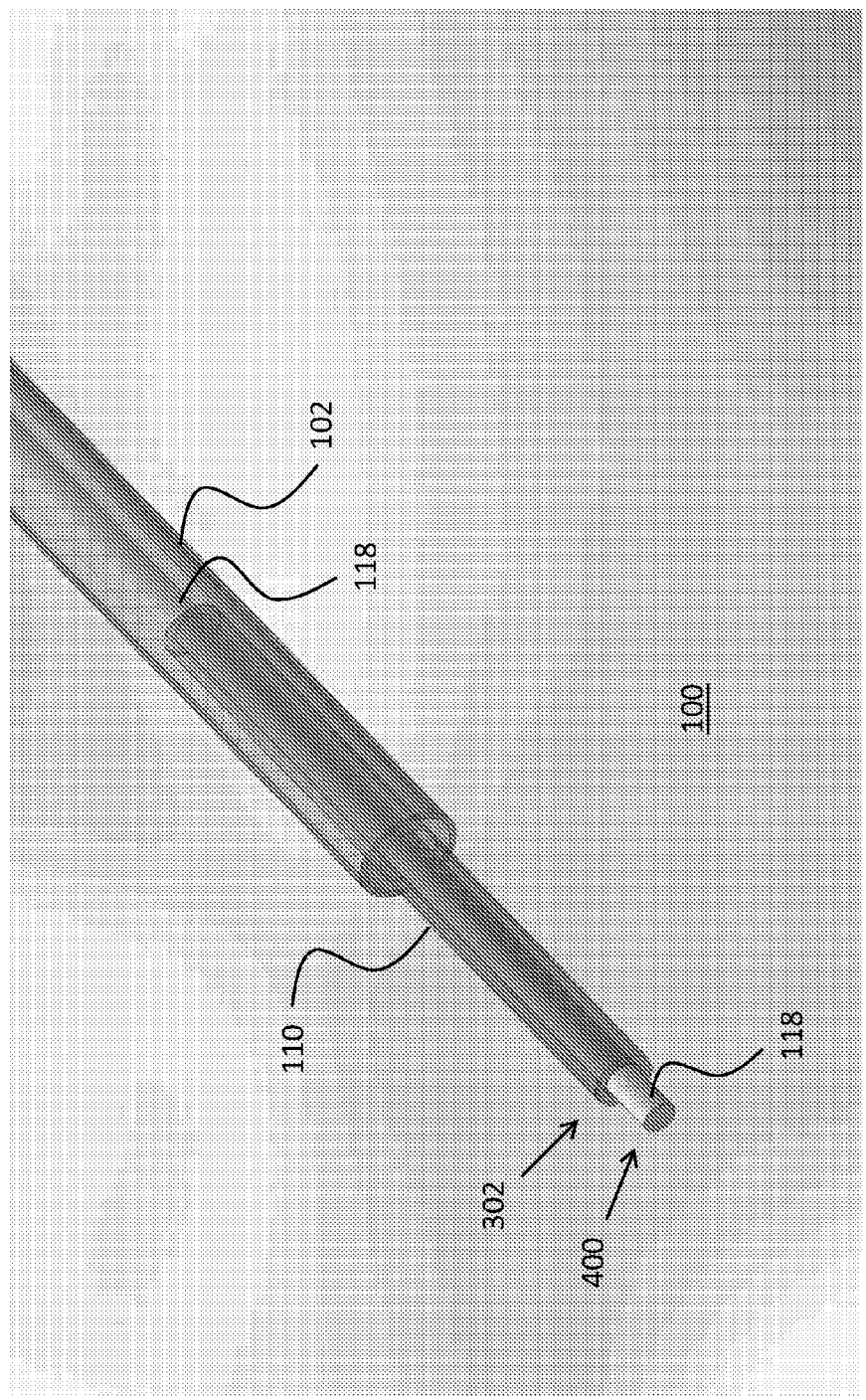
FIG. 4 is a fragmentary, transparent perspective view of the anti-clogging catheter device of FIG. 1 showing a stylet filling the material entry point shown in FIG. 3.

In accordance with an embodiment of the present invention, as shown in FIG. 4, the solid stylet 118 is configured to move and slide distally within the cannula 102 and into and through the tip 110 until the distal end 400 of the stylet 118 is at or extends beyond the distal end 302 of the tip 110. If the stylet 118 is dimensioned so that the outer diameter of the stylet 118 is substantially equal to the interior diameter of the tip 110, biological material is advantageously prevented from being excised from its biological source (e.g., the human brain) by preventing it from passing into the tip 110 as the solid stylet fills the passageway of the tip 110. "Substantially equal to," as used herein, indicates two objects that fit together with a close tolerance. In each case, substantially equal to indicates a stylet with an exterior dimension that allows it to tightly fit within one other object sufficient to prevent biological material from passing between the two objects. Once the anti-clogging catheter 100 is at the treatment site, the stylet 118 is simply slid back to the position shown in FIG. 1, and the fluid path 200 is once again established.

Figure 5:
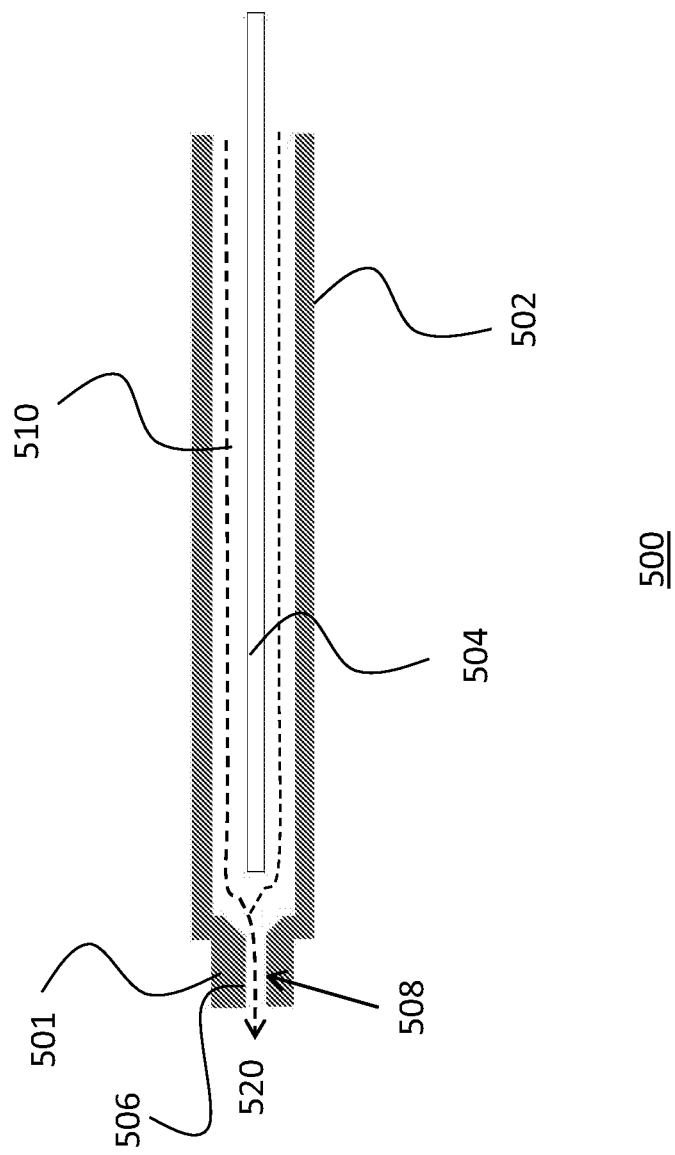
FIG. 5 is a longitudinal cross-sectional view of an exemplary embodiment of an anti-clogging catheter device having a tip extending beyond a cannula, distally-sloping internal transition areas, and a fluid-flow path in accordance with the present invention.

FIG. 5 shows a longitudinal cross-sectional view of a catheter 500 in accordance with an embodiment of the present invention. As with the anti-clogging catheter 100 shown in FIGS. 1-4, a tip 501 is inserted and fixedly coupled within a cannula 502 (of course, in each embodiment described herein, the tip can be integral with the cannula in which it resides). A solid stylet 504 is dimensioned so that its outer diameter is substantially equal to the interior diameter 506 of the tip 501. In the withdrawn position of FIG. 5, the stylet 504 does not block the fluid passageway 508 of the tip 501 and a stream of fluid 510 easily flows out of the device into a treatment area 520. However, as is shown in the cross-sectional view of FIG. 6, when the stylet 504 is slid in a distal direction and blocks and fills the fluid passageway 508, biological material is advantageously prevented from being excised from its biological source (e.g., the human brain) by preventing it from passing into the fluid passageway 508. If the stylet 504 is dimensioned so that the outer diameter of the stylet 504 is substantially equal to the interior diameter of the tip 501, biological material is advantageously prevented from passing into the tip 501. Even though the stylet 504 is illustrated as extending out of the tip 501 in FIG. 6, it can be limited to only extend to the distal limit of the tip 501 if desired.

Figure 6:
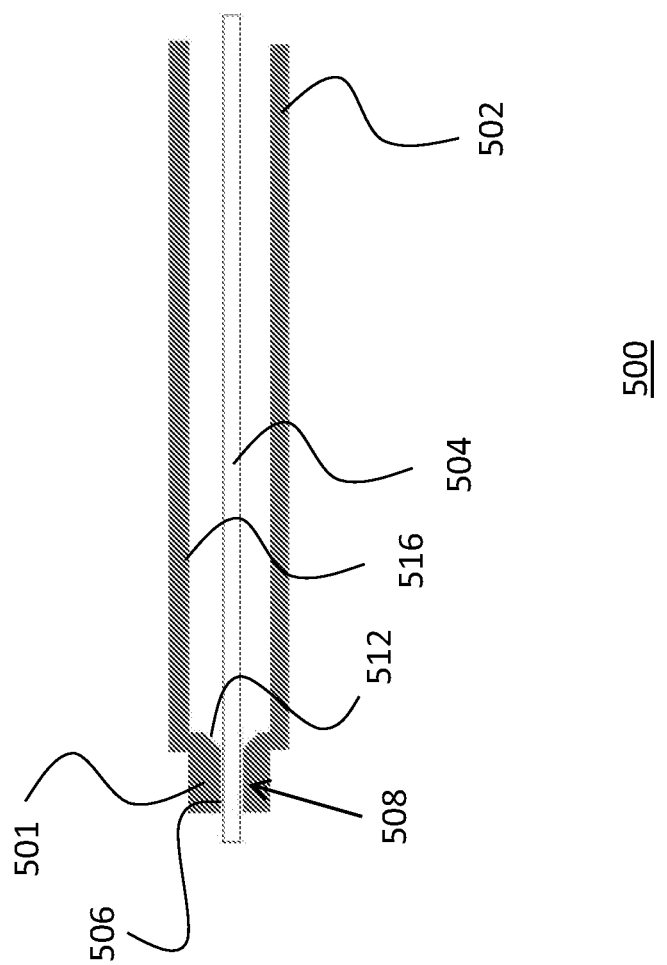
FIG. 6 is a longitudinal cross-sectional view of the anti-clogging catheter device of FIG. 5 showing a stylet filling a material entry point in accordance with the present invention.

The cross-sectional views of FIGS. 5 and 6 show an additional advantageous feature of the present invention. Between the passageway 508 of the tip 501 and the interior surface 516 of the cannula 502 is a distally-sloping transition region 512. The term "distally-sloping," as used herein, indicates a slope going from a larger-diameter opening of the device to a smaller-diameter opening, where the smaller-diameter opening is downstream from the larger-diameter opening in a fluid-delivery direction (see arrow head of illustrated fluid stream 510 in FIG. 5). The distally-sloping transition region 512 prevents alignment issues with the stylet 504 by guiding the stylet 504 into the fluid passageway 508 of the tip 501 as the stylet 504 is moved distally within the cannula 502, as is shown when moving from FIG. 5 to FIG. 6.

Figure 7:
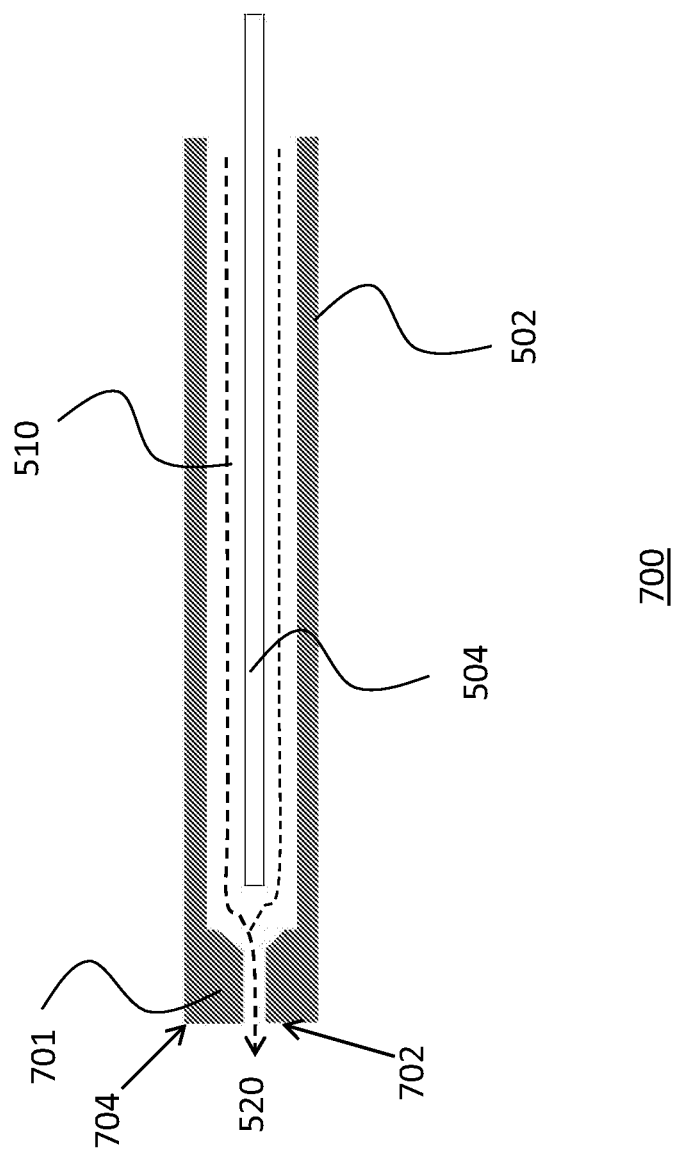
FIG. 7 is a longitudinal cross-sectional view of an exemplary embodiment of an anti-clogging catheter device having an aligned tip and cannula with distally-sloping internal transition areas and a fluid-flow path in accordance with the present invention.
Figure 8:
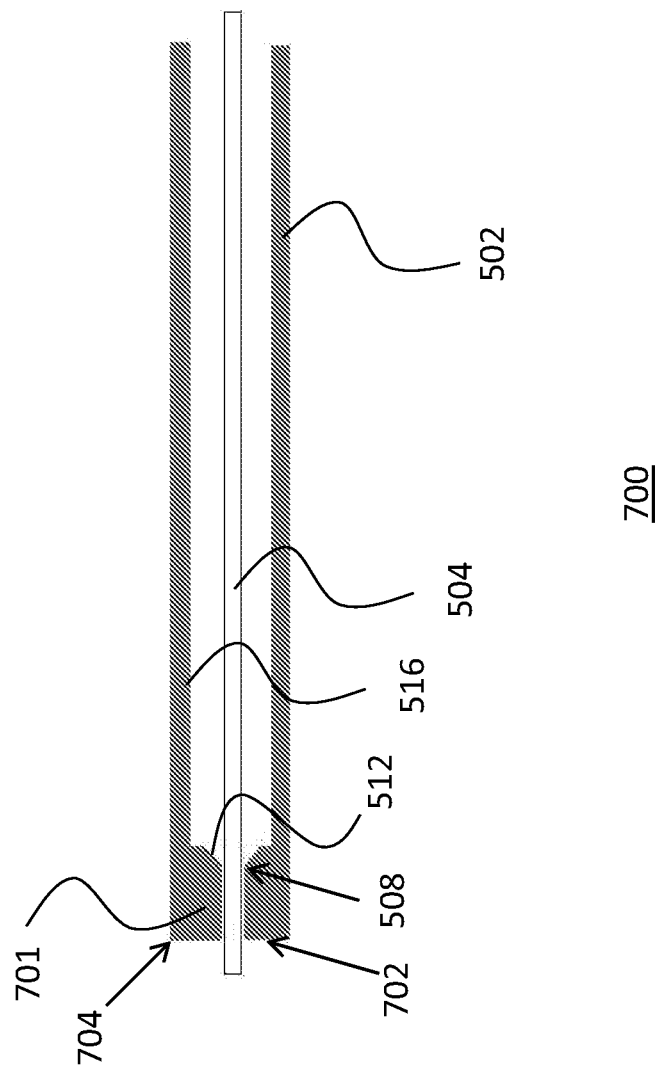
FIG. 8 is a longitudinal cross-sectional view of the anti-clogging catheter device of FIG. 7 showing a stylet filling a material entry point in accordance with the present invention.

FIGS. 7 and 8 provide another illustrated embodiment of a catheter 700 of the present invention. A difference between the embodiment of FIGS. 7 and 8 and that of FIGS. 5 and 6 is that, in the embodiment of FIGS. 7 and 8, the distal end 702 of the tip 701 and the distal end 704 of the cannula 502 are aligned with each other (i.e., co-planar). In other words, the embodiment of FIGS. 7 and 8 is structurally similar to that shown in FIGS. 5 and 6, except that the tip 701 does not extend beyond a distal extent 704 of the cannula 502. If the solid stylet 504 is dimensioned so that the outer diameter of the stylet 504 is substantially equal to the interior diameter of the tip 701, biological material is advantageously prevented from being excised from its biological source (e.g., the human brain) by preventing it from passing into the tip 701 as the solid stylet fills the passageway of the tip 701. As above, even though the stylet 504 is illustrated as extending out of the tip 701 in FIG. 8, it can be limited to only extend to the distal limit of the tip 701 if desired.

Figure 9:
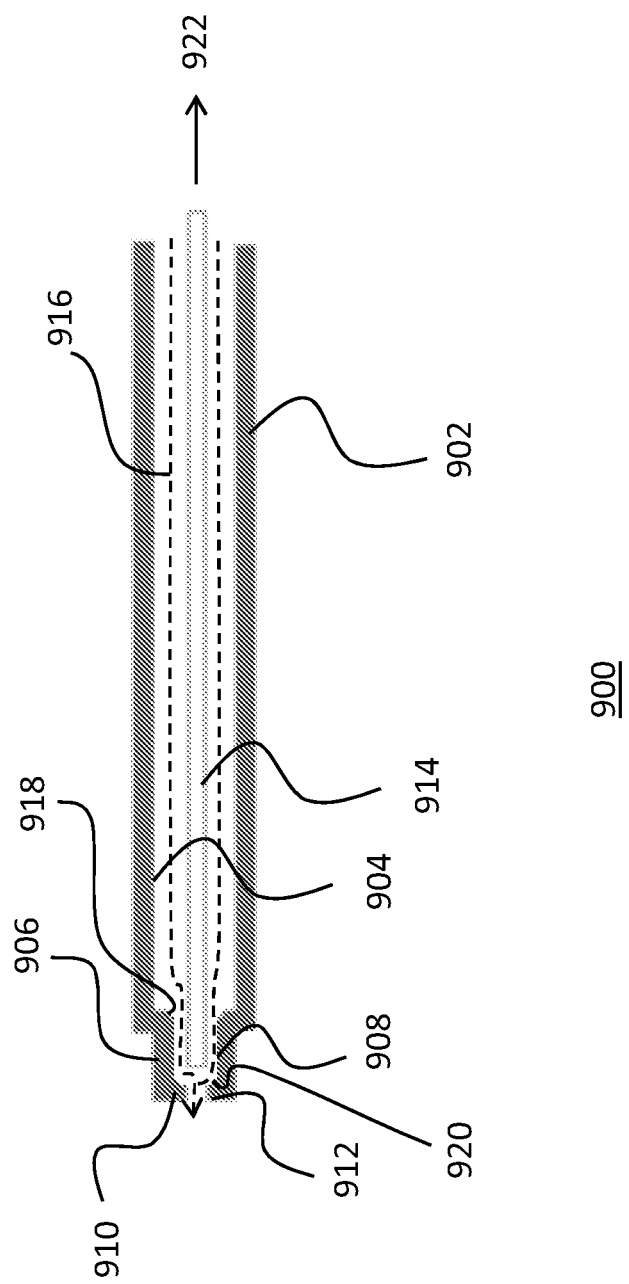
FIG. 9 is a longitudinal cross-sectional view of an exemplary embodiment of an anti-clogging catheter device having a tip extending beyond a cannula, an orifice aligned with an end of the tip, distally-sloping internal transition areas, and a fluid-flow path, in accordance with the present invention.

FIG. 9 shows another embodiment of an anti-clogging catheter in accordance with the present invention. Here, the catheter 900 includes a cannula 902 having an interior surface 904 defining an interior diameter. A tip 906 is fixedly coupled to the interior surface 904 of the cannula 902. The tip 906 has an interior surface 908 that defines a tip interior diameter. As in the previously-described embodiments of FIGS. 1-8, the interior diameter of the tip 906 is less than the interior diameter of the cannula 902.

Additionally, an orifice 910 is fixedly coupled to the catheter 900 so that it resides within the interior surface 908 of the tip 906 (it can be integral as well). The orifice 910 has its own interior surface 912 that defines an aperture for passing fluid out or into the catheter. The aperture has a diameter that is less than the interior diameter of the tip 906 but not less than the outer diameter of the solid stylet 914.

In the embodiment depicted in FIG. 9, as in each of the embodiments described thus far, a stylet 914 is slidable within the interior of the cannula 902. Here, as shown in FIG. 10, the stylet 914 is also slidable within the tip 906 as well as within the orifice 910.

In this embodiment, the solid stylet 914 has an outer diameter that is substantially equal to the interior diameter of the orifice 910. Due to the close tolerance between the outer diameter of the stylet 914 and the interior diameter of the orifice 910, biological material is prevented from being excised from its biological source (e.g., the human brain) by preventing it from passing through the orifice 910 and into the device as the solid stylet fills the orifice 910. Clogging of the catheter is thereby advantageously avoided. Once the device is inserted through the biological material to the treatment site, the stylet 914 is withdrawn and a fluid path 916 is established. A comparison of the embodiment of FIGS. 9 and 10, which features an orifice 910, to the other so-far illustrated and described embodiments shows that the orifice 910 is advantageous in that the stylet 914 does not need to be withdrawn as far in the proximal direction 922 for a fluid flow path to open up. Although the embodiments shown and described are not necessarily of an accurate scale and do not limit the invention, the orifice 910 is envisioned as being laterally shorter than the tips 110, 501, 701.

Figure 10:
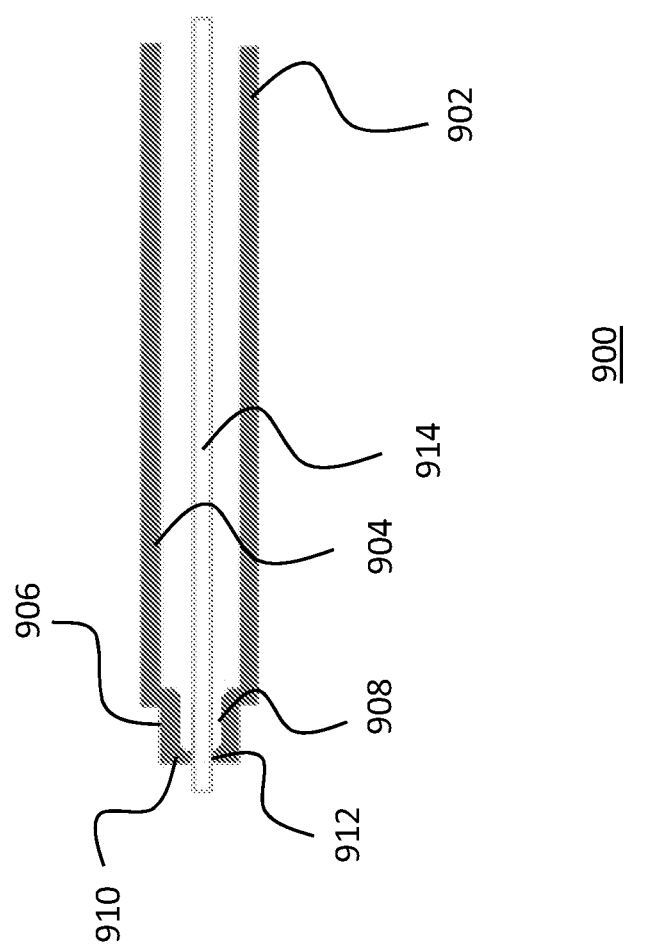
FIG. 10 is a longitudinal cross-sectional view of the anti-clogging catheter device of FIG. 9 showing a stylet filling a material entry point in accordance with the present invention.

The side elevational views of FIGS. 9 and 10 show an additional advantageous feature of the present invention. Between the passageway defined by the interior surface 908 of the tip 906 and the passageway defined by the interior surface 904 of the cannula 902 is a distally-sloping transition region 918. Again, the term "distally-sloping," as used herein, indicates a slope going from a larger-diameter opening of the device to a smaller-diameter opening, where the smaller-diameter opening is downstream from the larger-diameter opening in a fluid-delivery direction. The distally-sloping region 918 guides the stylet 914 into the fluid passageway defined by the interior surface 908 of the tip 906 when the stylet 914 is moved distally within the cannula 902.

Furthermore, between the passageway defined by the interior surface 912 of the orifice 910 and the passageway defined by the interior surface 908 of the tip 906 is a distally-sloping transition region 920. The distally-sloping region 920 guides the stylet 914 into the fluid passageway defined by the interior surface 912 of the orifice 910 when the stylet 914 is moved distally within the tip 906. If the stylet 914 is dimensioned so that the outer diameter of the stylet 914 is substantially equal to the interior diameter of the tip 906, biological material is advantageously prevented from passing into the tip 906. Even though the stylet 914 is illustrated in FIG. 10 as extending out of the tip 906, it can be limited to only extend to the distal limit of the tip 906 if desired.

Figure 11:
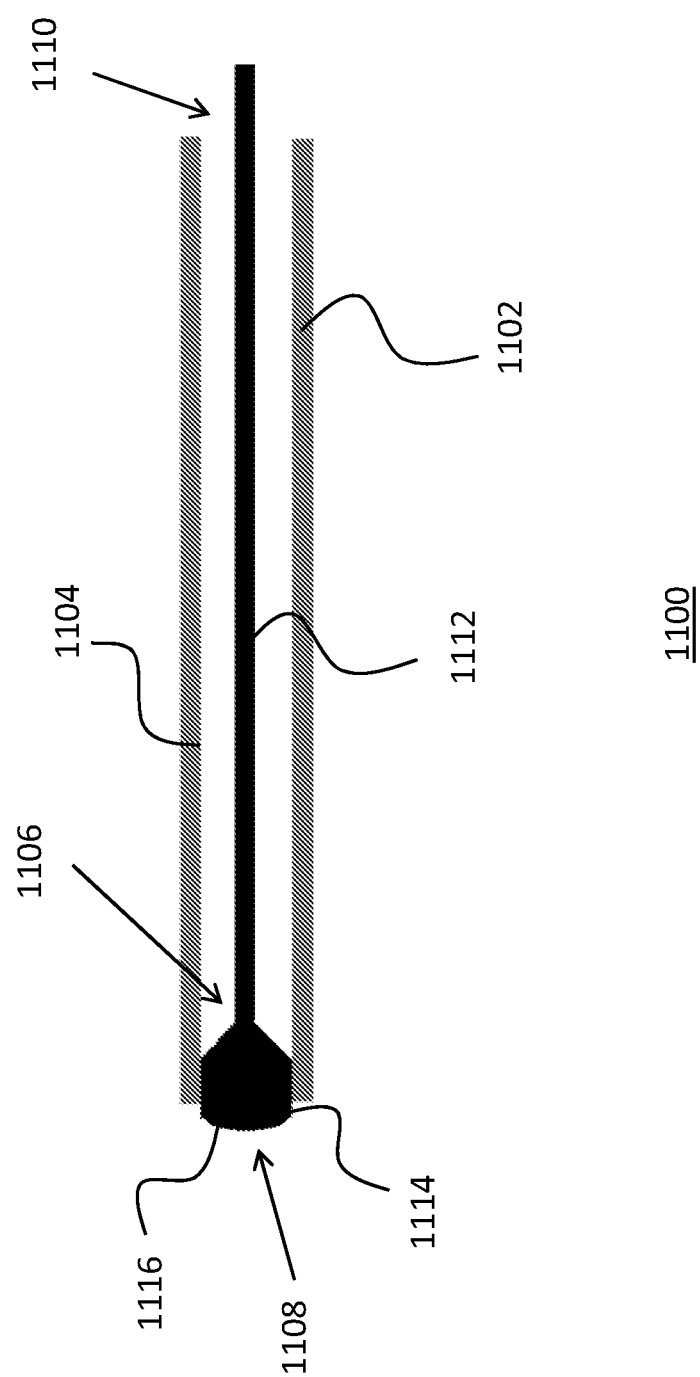
FIG. 11 is a longitudinal cross-sectional view of an exemplary embodiment of an anti-clogging catheter device having a stylet filling a material entry point in accordance with the present invention.

FIG. 11 shows yet another embodiment of an anti-clogging catheter 1100 according to the present invention. The embodiment of FIG. 11 features a cannula 1102 with an interior surface 1104 defining an interior diameter. A stylet 1106 is movable within the cannula 1102 and has a proximal end 1110 and a distal end 1108. A first exterior surface 1112 of the stylet 1106 defines a first exterior diameter that is less than the interior diameter of the cannula 1102. As will be shown in the following figure, the difference between the exterior diameter of the stylet 1106 and the interior diameter of the cannula 1102 provides a fluid flow pathway 1200. Referring still to FIG. 11, the stylet 1106 features a head 1116 at the distal end 1108. The head 1116 has a second exterior surface 1114 that defines a second exterior diameter of the stylet 1106. The second exterior diameter of the stylet 1106 is greater than the first exterior diameter of the stylet 1106 and is substantially equal to the interior diameter of the cannula 1102. In the case of the stylet 1106 and cannula 1102 of FIG. 11, when the stylet 1106 is slidably positioned so that the head 1116 is within the interior surface 1104 of the cannula 1102, fluid flow is prevented through the cannula 1102.

Figure 12:
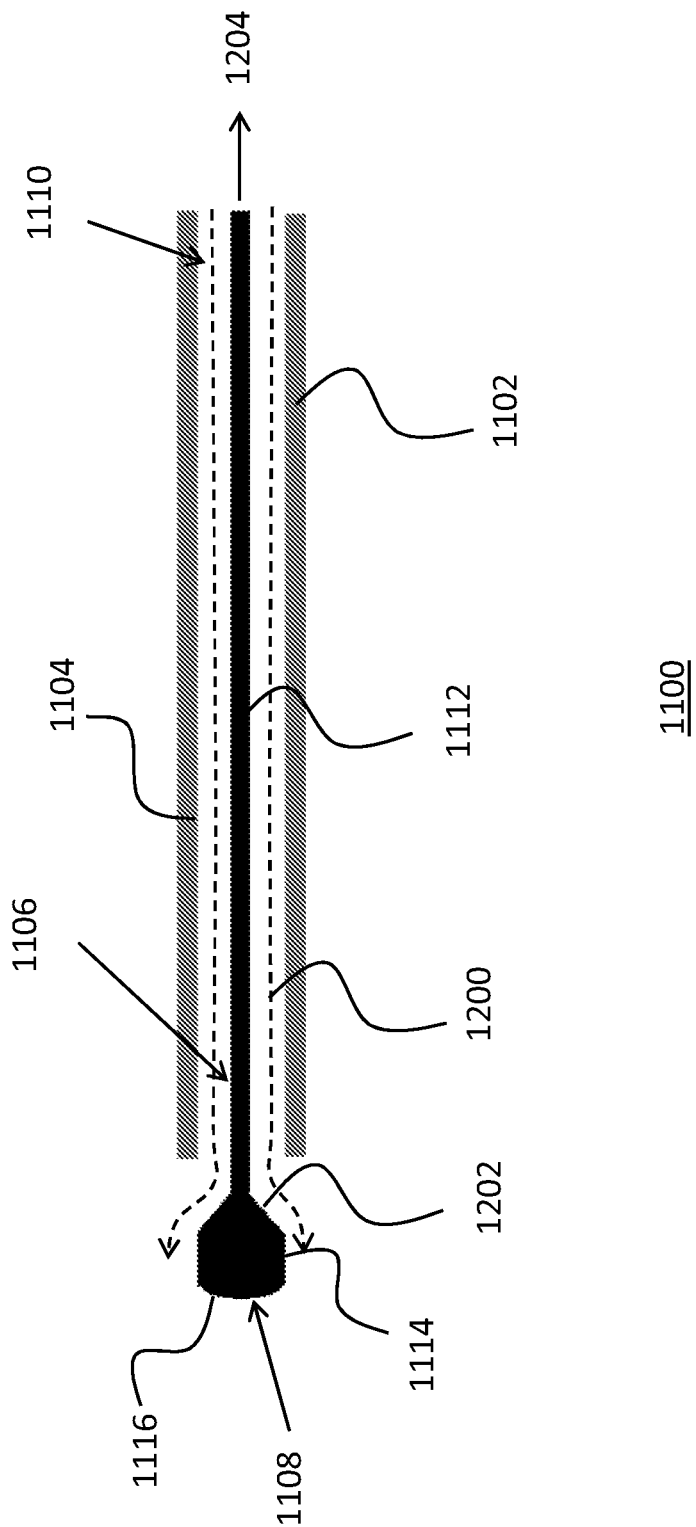
FIG. 12 is a cross-sectional elevational view of the anti-clogging catheter device of FIG. 11 with the stylet extended beyond a longitudinal limit of the cannula to create a fluid-flow path, in accordance with the present invention.

FIG. 12 shows the stylet 1106 moved forward, i.e., in a distal direction, with respect to the cannula 1102 so that the head 1116 is no longer within the interior of the cannula 1102. The separation of the head 1116 from the cannula 1102 opens a fluid path 1200 through the interior of the cannula 1102, around the head 1116, and to the treatment site. It should be noted that, because FIGS. 5-12 are cross-sectional views, the fluid paths 510, 916, and 1200 appear as two separate paths. However, in each of the embodiments described, round cannulas, tips, and stylets, as shown in FIGS. 1-3, are envisioned, and the separately appearing fluids paths actually are each a single contiguous fluid-flow path.

The stylet 1106 also features a proximally-sloping shoulder 1202 or transition region on a proximal side of the head 1116. The shoulder 1202 assists in aligning the head 1116 with the inner surface 1104 of the cannula 1102 when the stylet 1106 is pulled in the proximal direction 1204. The term "proximally-sloping," as used herein, indicates a slope going from a smaller-diameter outer surface of the device to a larger-diameter outer surface, where the larger-diameter surface is downstream from the smaller-diameter surface in a fluid-delivery direction.

In each of the embodiments described herein, the stylet 118, 504, 914, 1112 is solid and can be of materials such as, but not restricted to, a nickel titanium alloy, stainless steel, a fiber-optic material, a glass rod, a glass rod coated with polyimide, and others. Fiber-optic and glass materials have an advantage of being pliable while easily returning to their steady-state shape.

In each of the embodiments described herein, the cannula 102, 502, 902, and 1102 can be of materials such as, but not restricted to, silicone, fused silica, stainless steel, and others. For chronic applications, where insertion is expected to exceed one or more days, more flexible silicone is desirable. For acute applications, where insertion is expected to be less than a day, the more rigid materials, such as fused silica and stainless steel can be selected.

Figure 13:
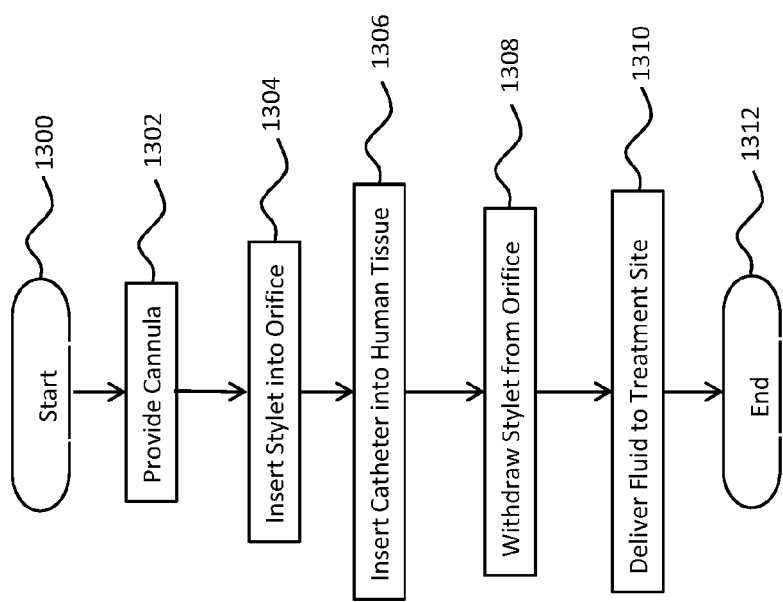
FIG. 13 is a process flow diagram illustrating a method for using an anti-clogging catheter in accordance with the present invention.

FIG. 13, in conjunction with FIGS. 9 and 10, shows an exemplary process flow diagram of a method for using an anti-clogging catheter 900 shaped and tipped to removably insert within and be removed from a human body. The process starts at step 1300 and moves directly to step 1302 where a cannula 902 having an interior surface 904 defining an interior diameter is provided. In a following step, 1304, as shown in FIG. 10, a stylet 914 is slidably inserted through the cannula 902, through the tip 906, and into the orifice 910 to fill and block an aperture in the orifice defined by the inner surface 912 and to prevent biological material from passing through the orifice 910. The stylet 914 can either extend out of the tip 906 or end at the distal surface of the tip 906. In step 1306, the catheter 900, with the orifice 910 blocked by the stylet 914, is inserted into human tissue, such a soft neurological tissue, until the orifice 910 reaches a treatment site. Once in place, in step 1308, the stylet 914 is withdrawn from the aperture of the orifice 910, as shown in FIG. 9. Once the stylet 914 is fully withdrawn from the aperture of the orifice 910, fluid is delivered along the fluid path 916 out of the orifice and into the treatment site in step 1310. The process ends at step 1312.

Figure 14:
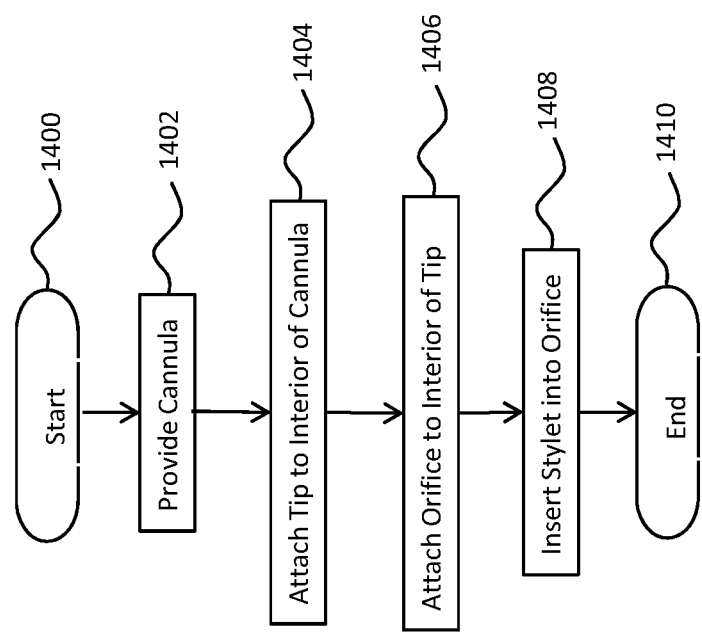
FIG. 14 is a process flow diagram illustrating a method for manufacturing an anti-clogging catheter in accordance with the present invention.

FIG. 14, in conjunction with FIGS. 9 and 10, shows an exemplary process flow diagram of a method for manufacturing an anti-clogging catheter 900 shaped and tipped to removably insert within and be removed from a human body. The process starts at step 1400 and moves directly to step 1402 where a cannula 902 having an interior surface 904 defining an interior diameter is provided. In step 1404, a tip 906 is fixedly coupled to, or made integral with, the interior surface 904 of the cannula 902. The tip 906 has an interior surface 908 defining a tip interior diameter that is less than the interior diameter of the cannula 902. Next, in step 1406, an orifice 910 is fixedly coupled to, or made integral with, the interior surface 908 of the tip 906. The orifice 910 has an interior surface 912 that defines an orifice interior diameter, which is less than the tip interior diameter. In a following step, 1408, as shown in FIG. 10, a solid stylet 914 is slidably inserted through the cannula 902, through the tip 906, and into the orifice 910 to fill and block an aperture in the orifice defined by the inner surface 912 and to prevent biological material from being excised from its biological source (e.g., the human brain) by preventing it from passing through the orifice 910. The process ends at step 1410.

Figure 15:
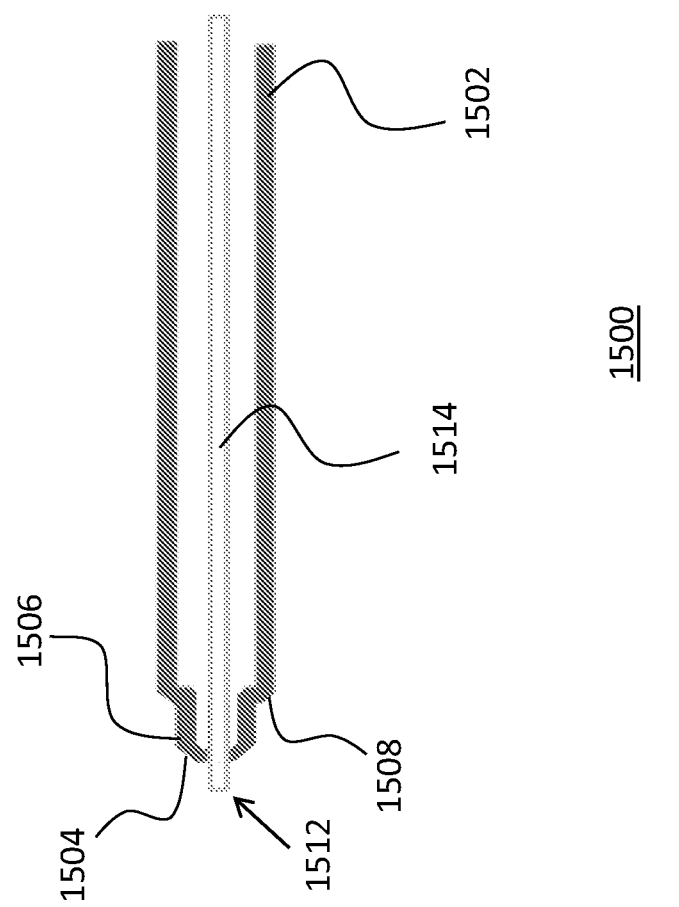
FIG. 15 is a longitudinal cross-sectional view of an exemplary embodiment of an anti-clogging catheter device having distally-sloping exterior transition regions.

FIG. 15 illustrates another exemplary embodiment of the present invention with a rounded shape on the distal tip 1512 of the solid stylet 1514. The rounded shape is useful in smoothly pushing through tissue as the catheter is being positioned in the treatment area. Furthermore, the present invention is also provided with a radius 1504 on the distal edges of the tip 1506. Like the rounded shape of the distal end 1512 of the solid stylet 1514, the radiused distal edge 1504 of the tip 1506 allows the inventive catheter 1500 to be smoothly positioned into the treatment area and minimize damage to the tissue being traversed. Of course, the cannula 1502 can also be provided with a radius 1508 on the distal edges of the cannula 1502.

What is claimed is:
1. An anti-clogging catheter comprising:
a hollow cannula defining a fluid passageway and shaped to removably insert within a human body, the cannula having:
a body portion having:
a proximal end;
a distal end opposite the proximal end;
a first interior surface defining a first interior diameter; and
an enclosed first exterior surface opposite the first interior surface, the first exterior surface spanning from the proximal end to the distal end of the body portion; and
a tissue-penetrating distal end having a second interior surface defining a second interior diameter smaller than the first interior diameter; and
a solid stylet movable within the fluid passageway and having an outer diameter substantially equal to the second interior diameter of the cannula, the stylet and cannula together defining:
a closed fluid pathway that prevents neurological material from passing into the tissue-penetrating distal end of the cannula when the distal end of the stylet is extended into the tissue-penetrating distal end of the cannula; and
an open fluid pathway that allows fluid to flow in a single contiguous path around the distal end of the stylet and out of the tissue-penetrating distal end of the cannula when the distal end of the stylet is retracted away from the tissue-penetrating distal end of the cannula and remains within the body of the cannula.

2. The anti-clogging catheter according to claim 1, further comprising:
a distally-sloping transition between the first interior surface and the second interior surface.

3. The anti-clogging catheter according to claim 1, wherein the distal end of the stylet comprises:
a rounded shape.

4. The anti-clogging catheter according to claim 1, wherein the cannula further comprises:
a third interior surface between the first interior surface and the second interior surface, the third interior surface having a third interior diameter smaller than the first interior diameter and larger than the second interior diameter.

5. The anti-clogging catheter according to claim 1, wherein the cannula has:
the first exterior surface radially opposite the first interior surface, the first exterior surface having the distal end;
a second exterior surface radially opposite the second interior surface, the second exterior surface having a proximal end; and
a radiused exterior surface between the first exterior surface and the second exterior surface.

6. The anti-clogging catheter according to claim 5, wherein the second exterior surface has a radiused distal edge.

7. The anti-clogging catheter according to claim 1, wherein:
the cannula is one of:
silicon
fused silica; and
stainless steel.

8. The anti-clogging catheter according to claim 1, wherein:
the stylet is one of:
fiber-optic;
glass rod;
nickel titanium; and
stainless steel.

9. The anti-clogging catheter according to claim 1, wherein the penetrating distal end comprises:
an edge with a radius.

10. An anti-clogging catheter comprising:
a solid stylet having a proximal end and a distal end;
a cannula surrounding the distal end of the stylet and:
having a body with a first interior surface defining a first interior diameter;
having a proximal end adjacent the proximal end of the stylet;
having a distal end with a second interior surface defining a second interior diameter smaller than the first interior diameter; and
having an enclosed first exterior surface opposite from and spanning a length of the first interior surface; and defining:
a closed fluid pathway that prevents neurological material from passing into the distal end of the cannula when the distal end of the stylet is extended into the distal end of the cannula; and
an open fluid pathway that allows fluid to flow in a single contiguous path around the distal end of the stylet and out of the distal end of the cannula when the closed end of the stylet is retracted away from the distal end of the cannula and remains within the body of the cannula.

11. The anti-clogging catheter according to claim 10, further comprising:
a distally-sloping transition between the first interior surface and the second interior surface.

12. The anti-clogging catheter according to claim 10, wherein the distal end of the stylet comprises:
a rounded shape.

13. The anti-clogging catheter according to claim 10, wherein the cannula further comprises:
a third interior surface between the first interior surface and the second interior surface, the third interior surface having a third interior diameter smaller than the first interior diameter and larger than the second interior diameter.

14. The anti-clogging catheter according to claim 10, wherein the cannula has:
the first exterior surface radially opposite the first interior surface, the first exterior surface having a distal end;
a second exterior surface radially opposite the second interior surface, the second exterior surface having a proximal end; and
a radiused exterior surface between the first exterior surface and the second exterior surface.

15. The anti-clogging catheter according to claim 10, wherein:
the cannula is one of:
silicon;
fused silica;
and stainless steel.

16. The anti-clogging catheter according to claim 10, wherein:
the stylet is one of:
fiber-optic;
glass rod;
nickel titanium; and
stainless steel.

17. An anti-clogging catheter comprising:
a hollow cannula shaped and tipped to removably insert within and be removed from a human body, the cannula having:
a distal end;
a proximal end;
an interior surface defining an interior diameter;
a hollow cannula interior; and
an enclosed exterior surface opposite the interior surface, the enclosed exterior surface spanning from the distal end to the proximal end; and
a stylet movable within the cannula and having:
a proximal end;
a distal end;
a first exterior surface at the proximal end defining a first exterior diameter less than the interior diameter of the cannula; and
a second exterior surface at the distal end defining a second exterior diameter, the second exterior diameter being greater than the first exterior diameter and substantially equal to the interior diameter of the cannula so that fluid flow is prevented through the distal end of the cannula upon the second exterior surface of the stylet being placed within the cannula interior.

18. The catheter according to claim 17, wherein the stylet further comprises:

a proximally-sloping transition between the first exterior surface and second exterior surface.

19. The catheter according to claim 17, wherein the stylet further comprises:
a rounded shape at the distal end.

20. The catheter according to claim 17, wherein the cannula further comprises:
a distal end having a radiused edge.

\* \* \* \* \*